(12) United States Patent
Wilson et al.

(10) Patent No.: US 10,806,581 B2
(45) Date of Patent: Oct. 20, 2020

(54) TETHERED IMPLANTABLE DEVICE HAVING AN APICAL BASE PLATE WITH A HYDRAULIC INTRACARDIAC ADJUSTING MECHANISM

(71) Applicant: Harmony Development Group, Inc., Cornelius, NC (US)

(72) Inventors: John Wilson, Cornelius, NC (US); Christopher Seguin, Norton, MA (US)

(73) Assignee: Harmony Development Group, Inc., Cornelius, NC (US)

( * ) Notice: Subject to any disclaimer, the term of this patent is extended or adjusted under 35 U.S.C. 154(b) by 34 days.

(21) Appl. No.: 15/987,430

(22) Filed: May 23, 2018

(65) Prior Publication Data

US 2019/0060076 A1 Feb. 28, 2019

Related U.S. Application Data

(60) Provisional application No. 62/509,976, filed on May 23, 2017, provisional application No. 62/509,905, filed on May 23, 2017.

(51) Int. Cl.
*A61F 2/24* (2006.01)
*A61F 2/06* (2013.01)
(Continued)

(52) U.S. Cl.
CPC ...... *A61F 2/2487* (2013.01); *A61B 17/12122* (2013.01); *A61B 17/12136* (2013.01);
(Continued)

(58) Field of Classification Search
CPC .... A61F 2/2487; A61F 2/2412; A61F 2/2433; A61M 1/12; A61M 1/122; A61M 1/1037; A61M 1/1086
(Continued)

(56) References Cited

U.S. PATENT DOCUMENTS 6,406,422 B1 * 6/2002 Landesberg ........ A61M 1/1072
600/17
6,827,682 B2 12/2004 Bugge et al.
(Continued)

FOREIGN PATENT DOCUMENTS

CN 106214289 A 12/2016
WO WO-2012/130052 A1 10/2012
(Continued)

OTHER PUBLICATIONS

International Search Report and Written Opinion for International Application No. PCT/US2018/034177 dated Jul. 20, 2018.
(Continued)

*Primary Examiner* — John R Downey
(74) *Attorney, Agent, or Firm* — Stephen J. Kenny; Robert Piston; Foley Hoag LLP (57) ABSTRACT

An implant system for restoring and improving physiological intracardiac flow in a human heart is provided including an implant for positioning at least partially within a human heart; an apical base plate assembly attachable to the apex of the heart; a tether assembly comprising a tether connected between the implant and the therapeutic apical base plate assembly, and an adjustment assembly connected to the tether assembly to permit longitudinal movement of the tether assembly and implant relative to the base plate assembly.

20 Claims, 12 Drawing Sheets

(51) Int. Cl.
| | |
|---|---|
| *A61F 2/48* | (2006.01) |
| *A61B 17/12* | (2006.01) |
| *A61B 17/00* | (2006.01) |
| *A61B 17/34* | (2006.01) |
| *A61B 90/00* | (2016.01) |

(52) U.S. Cl.
CPC .......... *A61F 2/2412* (2013.01); *A61F 2/2433* (2013.01); *A61F 2/2442* (2013.01); *A61B 17/00234* (2013.01); *A61B 2017/00017* (2013.01); *A61B 2017/00022* (2013.01); *A61B 2017/00221* (2013.01); *A61B 2017/00243* (2013.01); *A61B 2017/00539* (2013.01); *A61B 2017/00557* (2013.01); *A61B 2017/3425* (2013.01); *A61B 2090/036* (2016.02); *A61F 2002/068* (2013.01); *A61F 2002/482* (2013.01); *A61F 2002/485* (2013.01); *A61F 2210/009* (2013.01); *A61F 2220/0008* (2013.01); *A61F 2220/0033* (2013.01); *A61F 2220/0091* (2013.01); *A61F 2230/0013* (2013.01); *A61F 2250/0003* (2013.01); *A61F 2250/0013* (2013.01); *A61F 2250/0065* (2013.01); *A61F 2250/0069* (2013.01)

(58) Field of Classification Search
USPC .......................................................... 600/16
See application file for complete search history.

(56) References Cited

U.S. PATENT DOCUMENTS

| | | | |
|---|---|---|---|
| 7,435,257 B2 | 10/2008 | Lashinski et al. | |
| 7,854,762 B2 | 12/2010 | Speziali et al. | |
| 8,092,525 B2 | 1/2012 | Eliasen et al. | |
| 8,778,017 B2 | 7/2014 | Eliasen et al. | |
| 9,050,189 B2 | 6/2015 | Padala et al. | |
| 9,078,660 B2 | 7/2015 | Boutillette et al. | |
| 9,486,306 B2 | 11/2016 | Tegels et al. | |
| 9,498,330 B2 | 11/2016 | Solem | |
| 2003/0032855 A1 | 2/2003 | Shahinpoor | |
| 2006/0058871 A1 | 3/2006 | Zakay et al. | |
| 2006/0241745 A1* | 10/2006 | Solem | A61F 2/246 623/2.18 |
| 2007/0198082 A1 | 8/2007 | Kapadia et al. | |
| 2007/0265490 A1* | 11/2007 | Smith | A61M 1/1072 600/18 |
| 2007/0270943 A1 | 11/2007 | Solem et al. | |
| 2007/0282157 A1* | 12/2007 | Rottenberg | A61B 5/0215 600/16 |
| 2008/0064917 A1 | 3/2008 | Bar et al. | |
| 2008/0294251 A1* | 11/2008 | Annest | A61B 17/0401 623/3.1 |
| 2008/0306328 A1 | 12/2008 | Ercolani et al. | |
| 2009/0048668 A1 | 2/2009 | Wilson et al. | |
| 2009/0131849 A1 | 5/2009 | Maurer et al. | |
| 2009/0177028 A1 | 7/2009 | White | |
| 2009/0254195 A1* | 10/2009 | Khairkhahan | A61F 2/2487 623/23.67 |
| 2011/0022164 A1 | 1/2011 | Quinn et al. | |
| 2011/0196483 A1* | 8/2011 | Forsell | A61M 1/12 623/3.1 |
| 2011/0224655 A1 | 9/2011 | Asirvatham et al. | |
| 2013/0030519 A1* | 1/2013 | Tran | A61F 2/2433 623/2.11 |
| 2013/0172978 A1 | 7/2013 | Vidlund et al. | |
| 2013/0325110 A1 | 12/2013 | Khalil et al. | |
| 2014/0277404 A1* | 9/2014 | Wilson | A61F 2/2466 623/2.11 |
| 2014/0309732 A1* | 10/2014 | Solem | A61F 2/246 623/2.36 |
| 2014/0336751 A1 | 11/2014 | Kramer | |
| 2014/0371843 A1 | 12/2014 | Wilson et al. | |
| 2014/0371846 A1 | 12/2014 | Wilson et al. | |
| 2015/0073539 A1* | 3/2015 | Geiger | A61F 2/2439 623/2.11 |
| 2015/0112429 A1 | 4/2015 | Khairkhahan et al. | |
| 2015/0223934 A1* | 8/2015 | Vidlund | A61F 2/2457 623/2.11 |
| 2015/0245934 A1* | 9/2015 | Lombardi | A61F 2/2436 623/2.11 |
| 2016/0089234 A1 | 3/2016 | Gifford, III | |
| 2016/0089237 A1 | 3/2016 | Wilson et al. | |
| 2016/0113765 A1 | 4/2016 | Ganesan et al. | |
| 2016/0242909 A1 | 8/2016 | Ketai et al. | |
| 2016/0317290 A1* | 11/2016 | Chau | A61F 2/246 |
| 2017/0000935 A1 | 1/2017 | Vasilyev et al. | |
| 2017/0172737 A1 | 6/2017 | Kuetting et al. | |
| 2018/0015141 A1 | 1/2018 | Jay et al. | |
| 2018/0185145 A1 | 7/2018 | Wilson et al. | |
| 2018/0318071 A1 | 11/2018 | Lozonschi et al. | |
| 2018/0344461 A1 | 12/2018 | Wilson et al. | |

FOREIGN PATENT DOCUMENTS

| | | |
|---|---|---|
| WO | WO-2018/129312 A1 | 7/2018 |
| WO | WO-2018/129320 A1 | 7/2018 |
| WO | WO-2018/222894 A1 | 12/2018 |
| WO | WO-2019/006152 A1 | 1/2019 |
| WO | WO-2019/173385 A1 | 9/2019 |

OTHER PUBLICATIONS

International Search Report and Written Opinion for International Application No. PCT/US2018/012586 dated Mar. 20, 2018.
International Search Report and Written Opinion for International Application No. PCT/US2018/034174 dated Jul. 27, 2018.
International Search Report and Written Opinion for International Application No. PCT/US2018/040066 dated Sep. 12, 2018.
International Search Report and Written Opinion for International Application No. PCT/US2018/035427 dated Jul. 27, 2018.
International Search Report and Written Opinion for International Application No. PCT/US19/20816 dated Jul. 9, 2019.
International Search Report and Written Opinion for International Application No. PCT/US2018/12578 dated Mar. 28, 2018.

* cited by examiner

TETHERED IMPLANTABLE DEVICE HAVING AN APICAL BASE PLATE WITH A HYDRAULIC INTRACARDIAC ADJUSTING MECHANISM

CROSS-REFERENCE TO RELATED APPLICATIONS

This application claims the benefit under 35 USC § 119(e) of U.S. Provisional Application Ser. Nos. 62/509,976 and 62/509,905 filed May 23, 2017, which are hereby incorporated by reference in its entirety.

TECHNICAL FIELD

The present disclosure relates generally to an adjustment assembly for axial adjustment of an implant within a human heart for restoring and improving physiologic intracardiac flow and utilizing native force via force transduction.

SUMMARY

An implant system for restoring and improving physiological intracardiac flow in a human heart is provided including an implant for positioning at least partially within a human heart; a therapeutic force transferring and re-purposing apical base plate assembly attachable to the apex of the heart; a force transferring tether or shaft assembly comprising a tether or shaft connected between the therapeutic apical base plate assembly and the adjustment assembly; and an adjustment assembly connected to the tether assembly to permit longitudinal movement of the tether or shaft assembly and a distal implant relative to the base plate assembly. In effect, the tether or shaft and the base plate form a platform system for the delivery and re-purposing of native energy and force and the conversion of that energy and force into a restorative therapy.

In some embodiments, wherein the adjustment assembly includes a piston and/or a chamber and/or a piston in a chamber connected to the force transferring tether or shaft assembly. In some embodiments, the adjustment assembly maintains the longitudinal position of the piston until a pre-set force is exceeded by a native or external force in or of the heart. In some embodiments, the adjustment assembly provides controllable longitudinal movement of the piston.

In some embodiments, the adjustment assembly includes at least one of a spring, fluidic valving, mechanical valving, electrical valving, and magnetic valving.

In some embodiments, the adjustment assembly includes a fluid-filled body, wherein the piston is longitudinally moveable within the body and defines a fluid reservoir on each side of the piston. The longitudinal position of the piston can be adjustable by varying relative pressure in the fluid reservoirs.

BRIEF DESCRIPTION OF THE DRAWINGS

The objects, features and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein.

DETAILED DESCRIPTION

Figure 1:
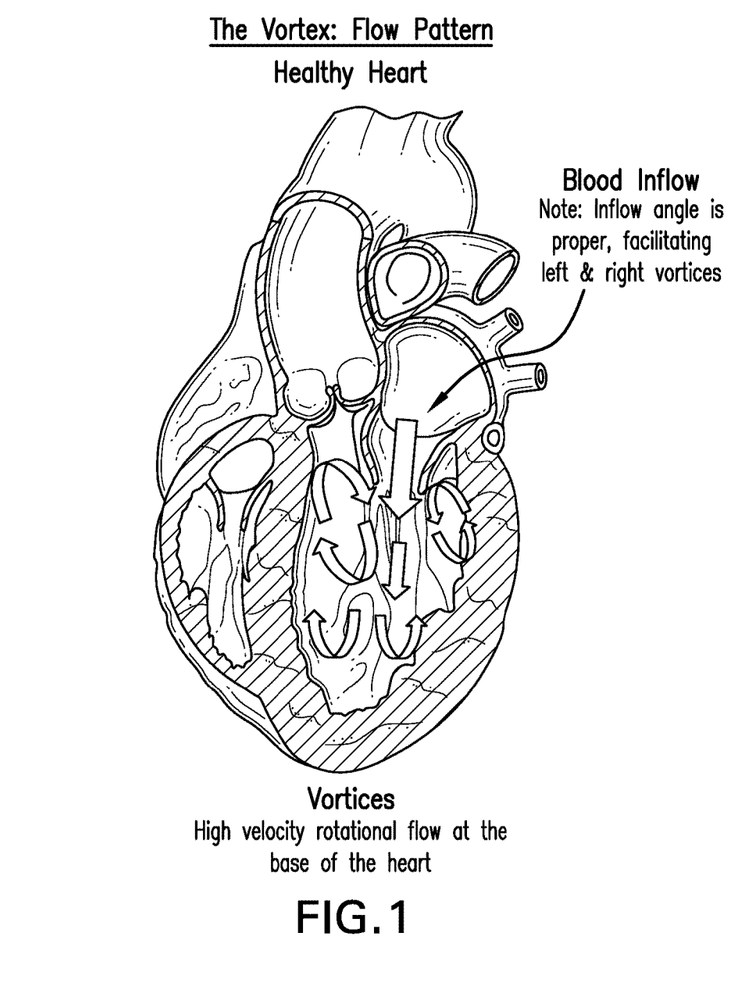
FIG. 1 is a diagram illustrating the vortex flow pattern of a healthy human heart.

One of the features of healthy heart function is proper physiological intracardiac flow. The atrioventricular pressure gradient, a force within a human heart, is defined as the pressure difference (or a pressure differential) that produces or generates energy and force within the chambers of the heart that occurs naturally. As the pressure increases in the atrium and the pressure reduces in the ventricle, called the diastolic phase or diastole, blood flows from the higher pressure atrium into the lower pressure ventricle causing the valve leaflets to open and thus allowing the blood to pass through the valve orifice. During the systolic phase or systole, the pressure in the atrium is exceeded by the pressure in the ventricle thereby generating a pressure differential creating an energy and force which, in turn, pushes up and against the valve leaflets causing them to close and seal off the ventricle from the atrial chamber. The atrioventricular pressure gradient is the driving energy and force required to close the valve. During systolic ventricular contraction, the considerable forces of the atrioventricular pressure gradient are exerted on the closed atrial/ventricular valve. Very importantly, these forces are transferred or transducted via the chordae tendinae and papillary muscles to and into the ventricular and septal walls. There is a resulting valvulo-ventricular wall interaction, which provides and enables the healthy ventricle to maintain structural integrity, to maintain healthy elliptical geometry, and provides functional support and structural stability for consistent healthy blood ejection. During ventricular diastole, the ventricular pressure rapidly decreases. The valve opens and blood rushes from the atrium into the ventricle through the valve orifice. The healthy valve leaflets function as a vector or steering mechanism, directing ventricular flow at an angle or vector to create vortical initial spin as illustrated in FIG. 1. Such angle or vector may be due to the asymmetry of the valve leaflets and/or to the different shapes and sizes of the leaflets. A critical vortex progression results. It is believed that the initial hemodynamic spin begins with inflowing blood, powered by the atrioventricular pressure gradient. On the ventricular side of the valve, the gradient pressure then engages that initial spin such that a vortex is created downstream. The resulting high velocity rotational flow, now a reservoir of kinetic energy within the ventricle is believed significant to proper blood flow velocity and volume through and out of the heart. By addressing, capturing, harnessing, delivering, and re-purposing a native force, that force being the atrioventricular pressure gradient, with a force re-purposing and transferring system consisting of a force transferring tether or shaft and a force transferring and delivering base plate assembly, a ventricular restoring therapy is achieved irrespective of any fluid volume which may appear in any other chamber of the heart. The structures of the heart are employed to harness and collect this energy and force and the energy and force then re-purposed utilizing the platform system described. The platform described employs the hearts structures to re-purpose a native and existing force and energy rather than assisting or aiding a failing structure such as a failing or an impaired heart valve.

Figure 2:
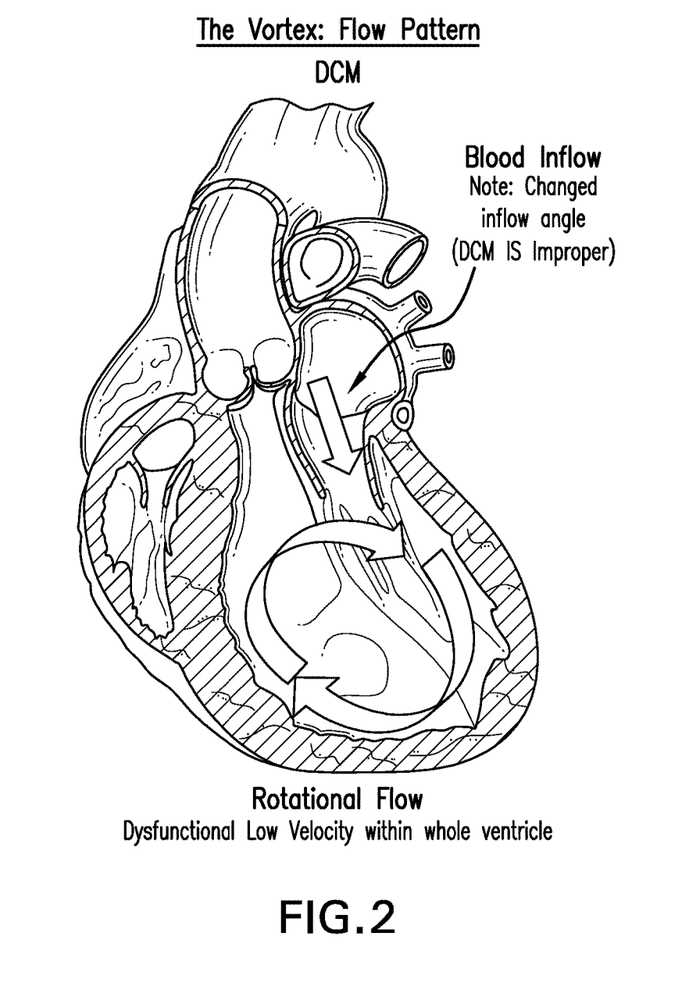
FIG. 2 is a diagram illustrating the dysfunctional vortex flow pattern of a human heart with pathology.

FIG. 2 illustrates that under certain conditions, such as a dilated cardiomyopathy (DCM) in which the heart becomes enlarged, the vortex fails to properly form, the elliptical shape is lost, the papillary muscles displace, and the ventricle is unable to pump blood efficiently. Such conditions are marked by a low velocity flow and poor cardiac output in which the vortices are abnormal or absent and geometric distortion is present creating flow and ventricular dysfunction.

In accordance with the disclosed subject matter, a flow vectoring member is implanted in the atrio-ventriclar space of the heart. It is connected to a tether or shaft anchored at the apex, and extends through the valve orifice into the atrium. When the ventricle contracts in systole, the member captures and harnesses the valvular and sub valvular energy and force of the atrioventricular pressure gradient by allowing the pressure differential to act on the exposed area of the member (meaning the valve leaflets and subvalvular apparatus seal and 'grab' onto the member). This transfers or transducts that energy and force, the atrioventricular gradient energy and force captured by the member, to the therapeutic force transferring apical base plate on and in contact with the apex, via the tethering conduit or shaft. When the ventricle relaxes in diastole, releasing the member, the structure and features of the flow vectoring member intercepts atrial blood and re-vectors it by channeling blood into the ventricle via the flow channel creating ribs or ridges. This enables or facilitates a changed or altered angle of flow or vector, assisting the initiation of vortex (i.e., spin) as blood flows off the leaflets and drains into the ventricle. By implanting the flow vectoring member, the normal intracardiac blood flow pattern that is disrupted by pathology or defect and unhealthy ventricular geometry can be restored and geometric distortion repaired via transduction or re-purposed native energy. This energy and force is delivered by the tether or shaft to therapeutic apical base plate and then into the ventricle and its structures thus restoring the valvulo-ventricular relationship and it's critical ventricular and septal wall interaction by contact.

An axial adjustment assembly optimizes atrial vectored outflow and ventricular vectored inflow as well as transducted forces of the atrioventricular pressure gradient by adjusting the intra-cardiac position of the flow vectoring member and harnessing the pressure differential and native forces by increasing or decreasing the exposed area, meaning in contact, of the implant. In some embodiments, longitudinal (axial) control is provided by a piston assembly attached to the tether or shaft. The piston acts to move the implant attached to the distal end of the tether or shaft, by moving the tether or shaft up or down, which facilitates the increased or decreased capture, harness, and transfer of energy and force (i.e., energy and force generated by a pressure differential between ventricle and atrium) and the valvulo-ventricular interaction of the valve components themselves to the apex, septal, and/or ventricular walls via transduction. This is achieved via or through the therapeutic apical base plate by increasing or decreasing the exposed surface area of the implant (by moving the implant up and/or down) to increase or decrease the amount of energy and force captured, harnessed, and transducted or moved. The piston acts to increase or decrease a force (e.g. cinching force) applied by an attached device or component within the heart as it moves axially or up & down.

In one embodiment, the member is an inflatable member, balloon, or paddle with flow channeling ribs or ridges. The paddle includes an internal cavity for filing with inflating liquid. Such fluid is passively redirected up and down in the flow vectoring member by cardiac contractions.

Figure 3:
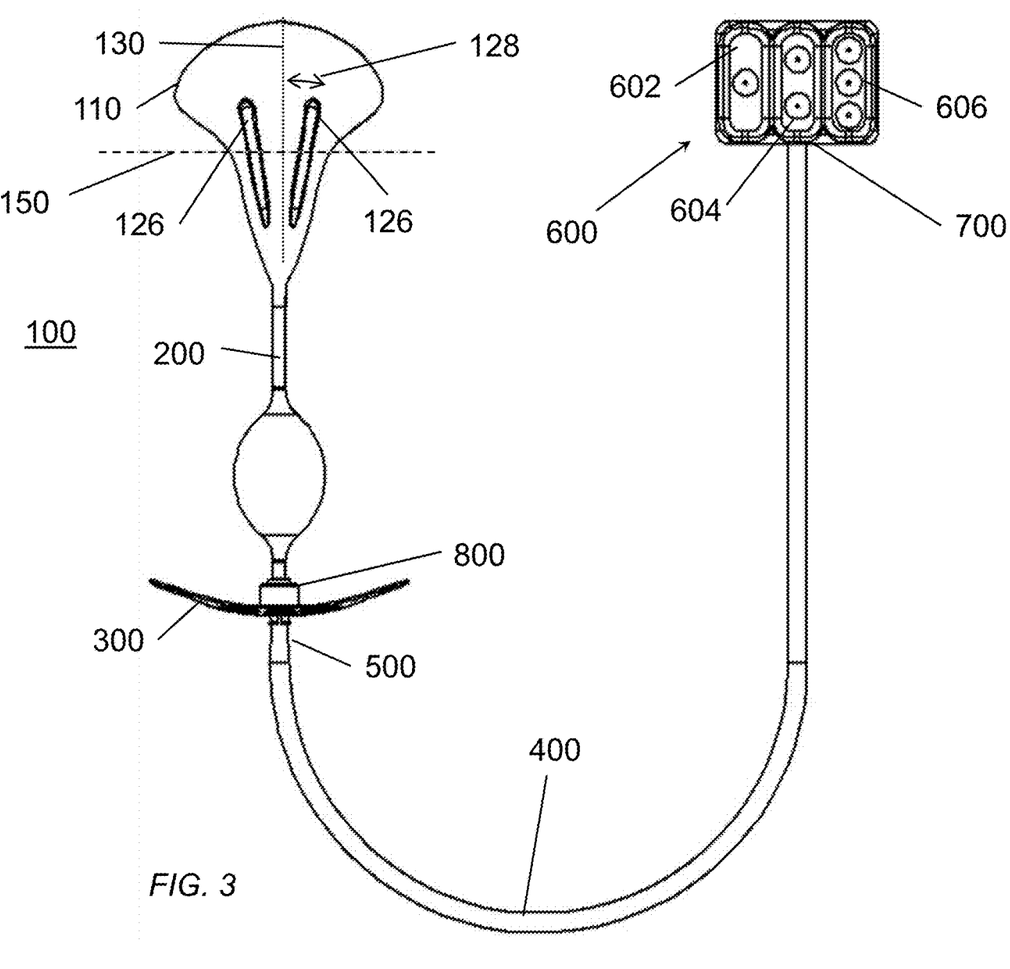
FIGS. 3-4 illustrate the system in accordance with exemplary embodiments of the disclosed subject matter.
Figure 4:
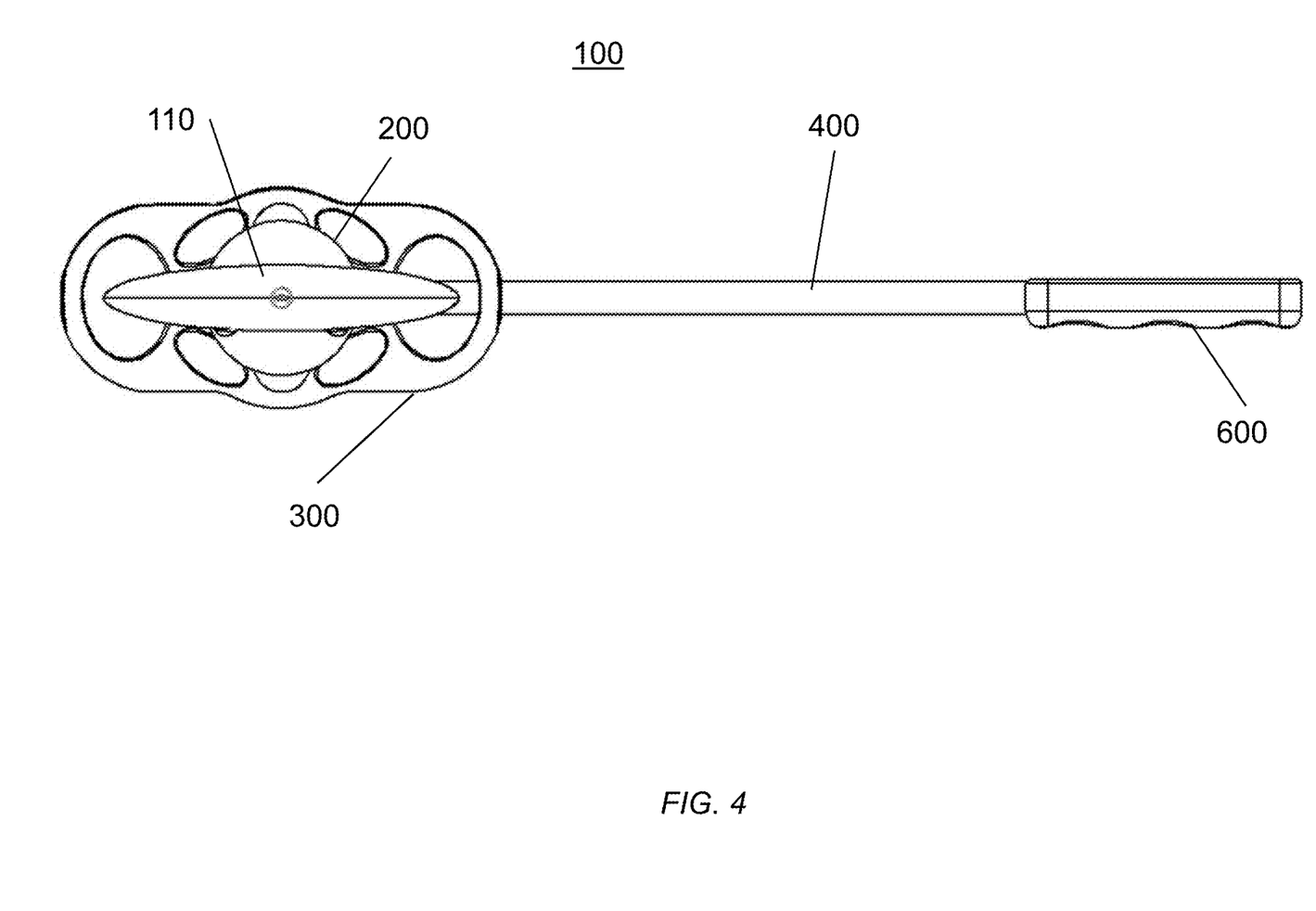
Figure 17:
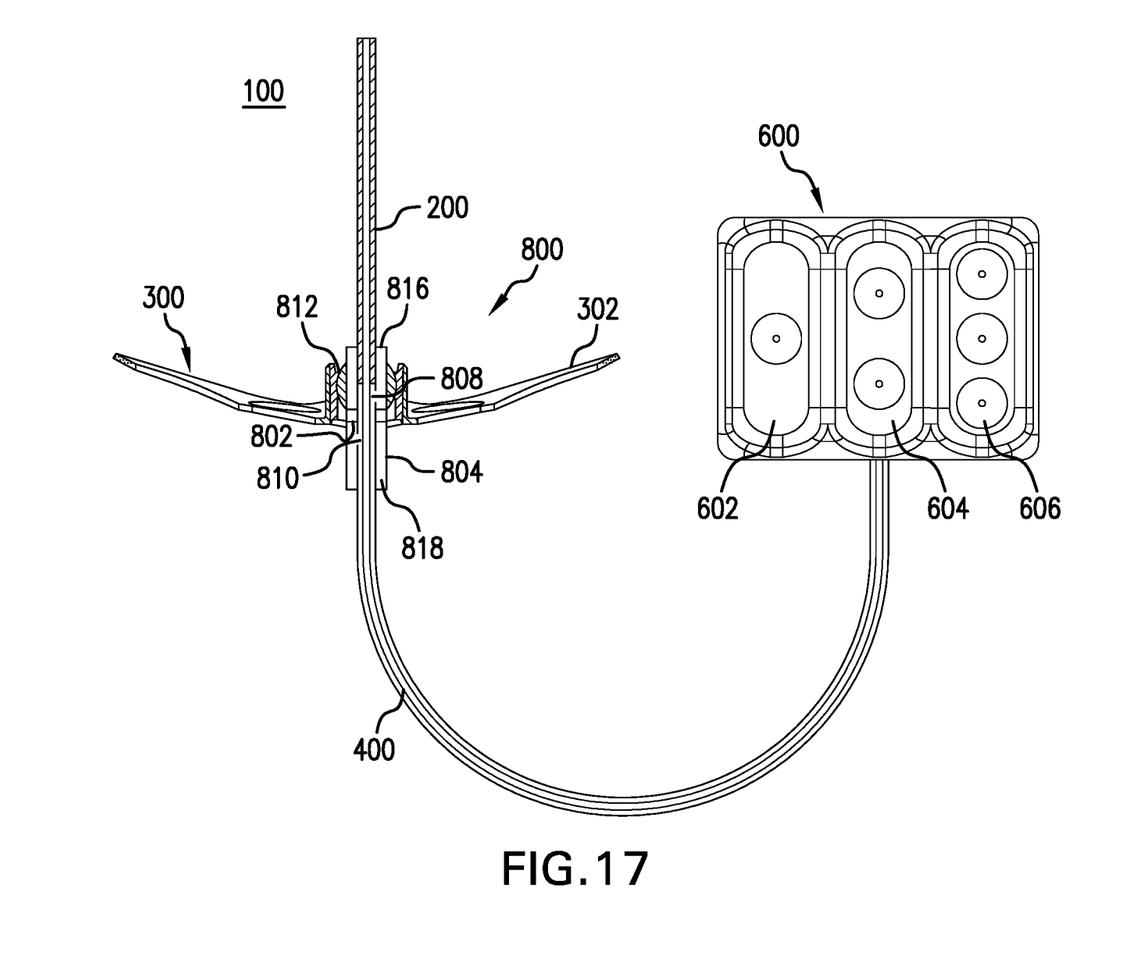
FIG. 17 is a side view in partial cross section of the system in accordance with exemplary embodiments of the disclosed subject matter.

As illustrated in FIGS. 3 and 4, the implant device 100 includes a flow vectoring member which may be a paddle, or a single, or multi chamber fluid filled member 110 connected to a multi-lumen transducting conduit or shaft 200 (or force transducting tether). The transducting shaft 200 is designed to be fixed to the apex A of the heart H by a therapeutic apical base plate assembly 300. (Implantation of the device 100 in the heart H is illustrated herein below in FIG. 19.) The transducting conduit or shaft 200 is connected to a multi lumen tube 400 after exiting the apex A at joint 500. Multi-lumen tube 400 is connected to a control unit 600 at connection 700. Control unit 600 adjusts the device performance via a fluid communicating system when connected to the multi lumen tube 400. FIG. 3 illustrates that approximation location of the line of coaptation by the valvular structure is denoted by dotted line 150. An adjustment assembly 800, illustrated in FIG. 17, provides longitudinal control of the intracardiac position of the implant 110, for example, adjusting the position of implant 110 relative to the valve. In some embodiments, the adjustment assembly maintains the longitudinal position of the piston until pre-set force is exceeded by a change in cardiac forces. In some embodiments, the adjustment assembly provides controllable longitudinal movement of the piston.

Figure 5:
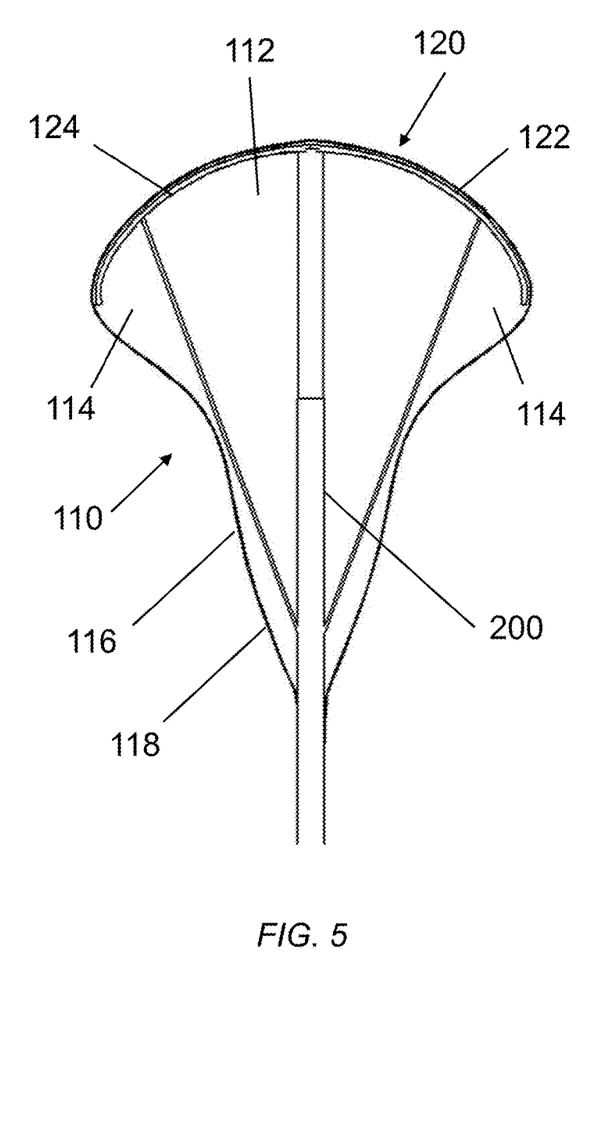
FIG. 5 is a cutaway side view of an implant member in accordance with exemplary embodiments of the disclosed subject matter.

The member 110 is illustrated in greater detail in FIG. 5, and is designed with exterior surfaces to intercept and redirect blood flow from the atrium AT to the ventricle VT.

The member 110 may have a wider "manta"-shape portion 112 including side wings 114 at distal end portion, that tapers towards a mid-portion 116 and further towards a narrow end portion 118. The "manta"-shape portion 112 is designed to be positioned in the atrium AT, and the mid portion 114 and narrower portion 116 are designed to be positioned through the valve V and into the ventricle VT. In some embodiments, member 110 includes a lateral ('wing to wing') shape support structure, e.g., a skeletal crescent beam 120, fixed to the distal end of the shaft 200 with two force-transducting trusses 124 connecting to the proximal end of the shaft 200 inside of the member 110 to aid in the transduction of captured atrioventricular pressure gradient energy and force as well as the interception and re-vector of atrial blood flow. The "manta"-shape portion 112 of the member 110 intercepts atrial blood and re-vectors it to enhance, facilitate, or restore proper blood flow vector by channeling blood via the flow channel creating ribs 126 and passing blood over and off of the valve leaflets and into the ventricle VT. The member 110 captures the native force of atrioventricular pressure gradient and the valvular and sub-valular structures V as they coapt or 'grab and pull' on the member 110 in systole. It is understood that member 110 represents one exemplary embodiment of a flow vectoring member or other device that may be used in connection with the adjustment assembly described herein. In other embodiments, the shaft may be attached at the distal end of the shaft to the proximal end of replacement valves, partial prosthetics or valves, regurgitation mitigation devices, and ventricular modification and therapeutic devices. (e.g., replacement valves, partial prosthetic valves, or regurgitation mitigation device).

Figure 6:
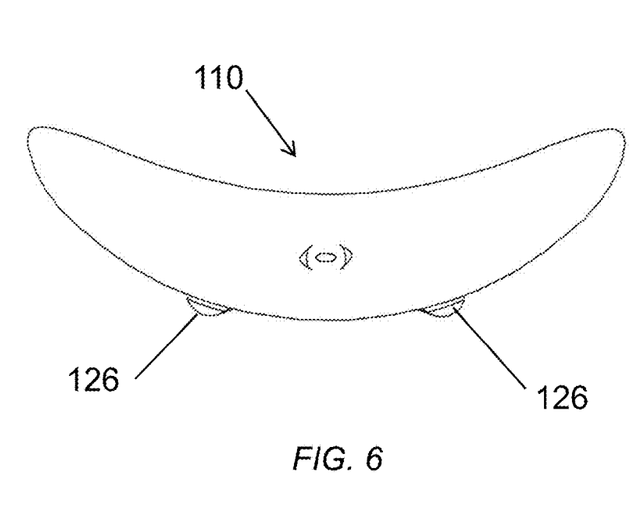
FIGS. 6 and 7 are distal end views of the implant member of FIG. 5 disposed in anterior and posterior articulation in accordance with exemplary embodiments of the disclosed subject matter.
Figure 7:
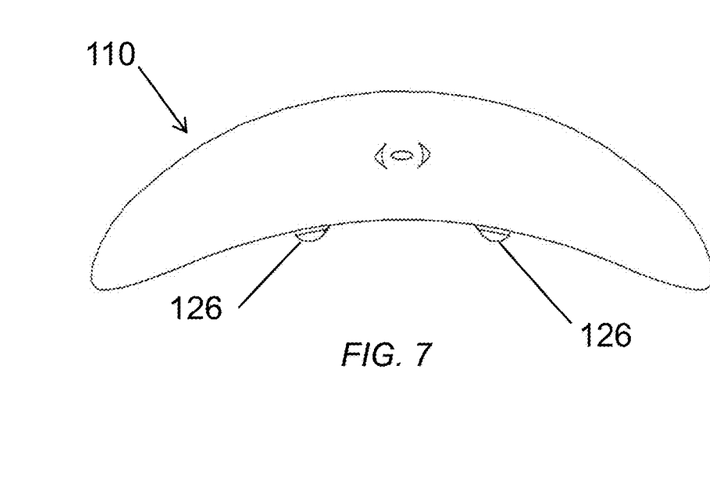
Figure 8:
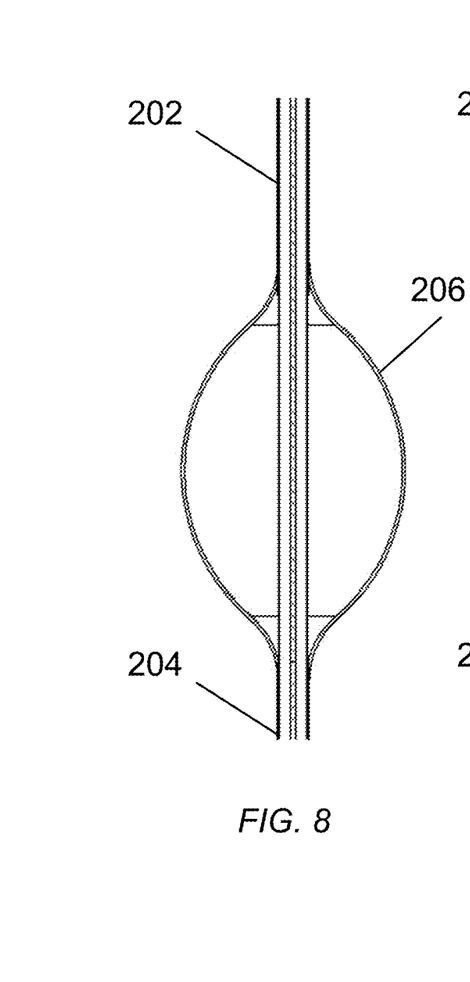
FIGS. 8-9 are axial views of the transducting conduit or shaft with the reservoir or balloon inflated in accordance with exemplary embodiments of the disclosed subject matter.
Figure 9:
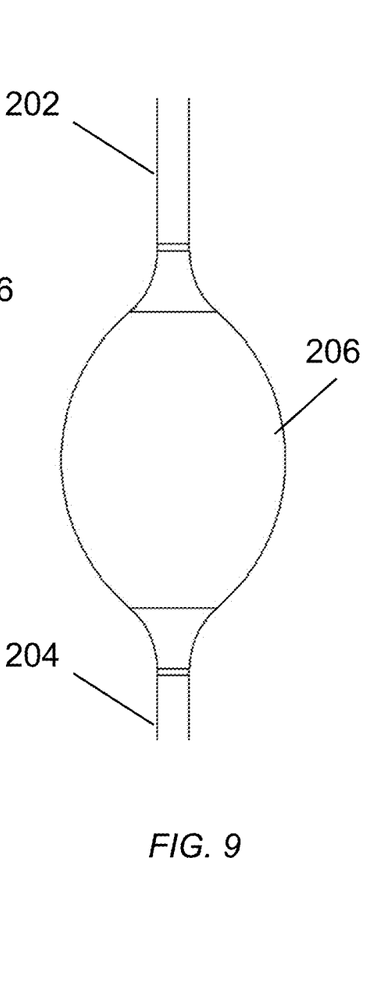
Figure 10:
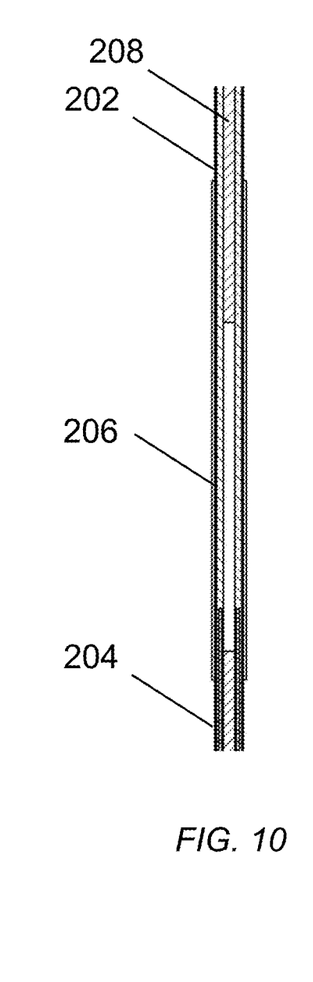
FIGS. 10-11 are axial views of the transducting conduit or shaft with the reservoir or balloon deflated in accordance with exemplary embodiments of the disclosed subject matter.
Figure 11:
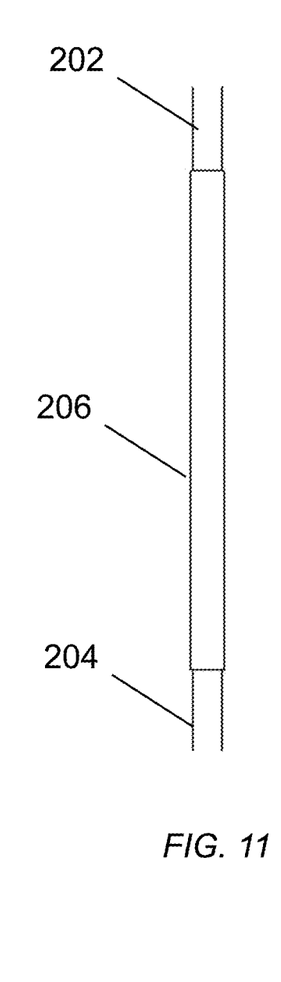
Figure 12:
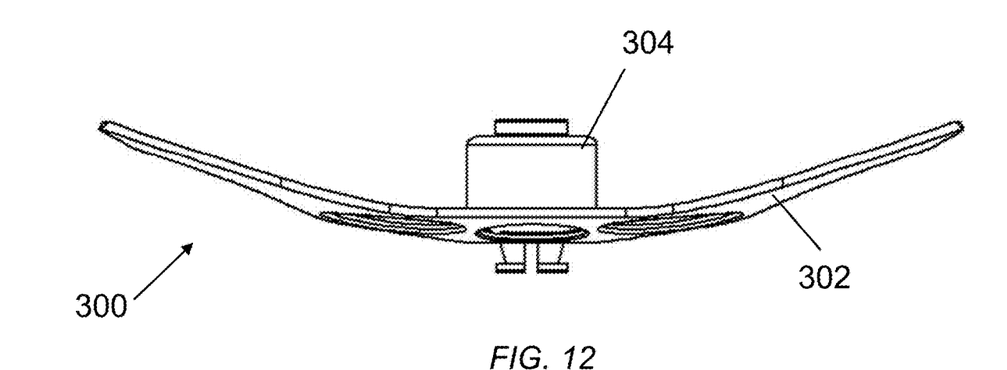
FIG. 12 is a side view of the therapeutic apical base plate assembly in accordance with exemplary embodiments of the disclosed subject matter.
Figure 13:
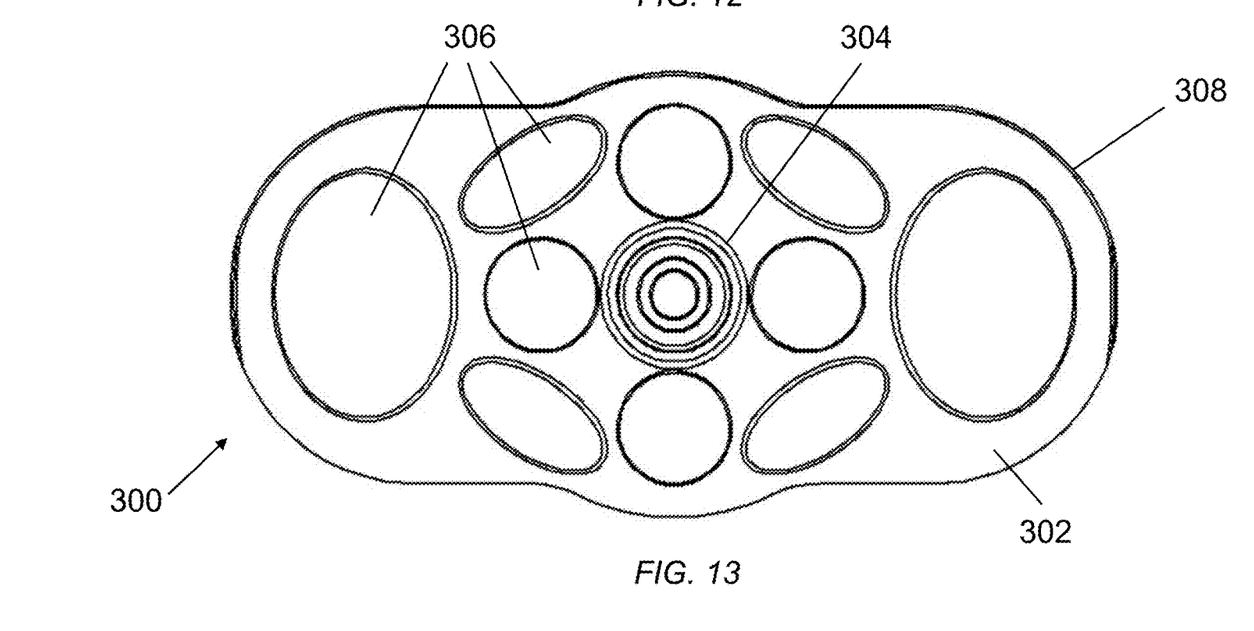
FIG. 13 is top view of the therapeutic apical base plate assembly in accordance with exemplary embodiments of the disclosed subject matter.
Figure 14:
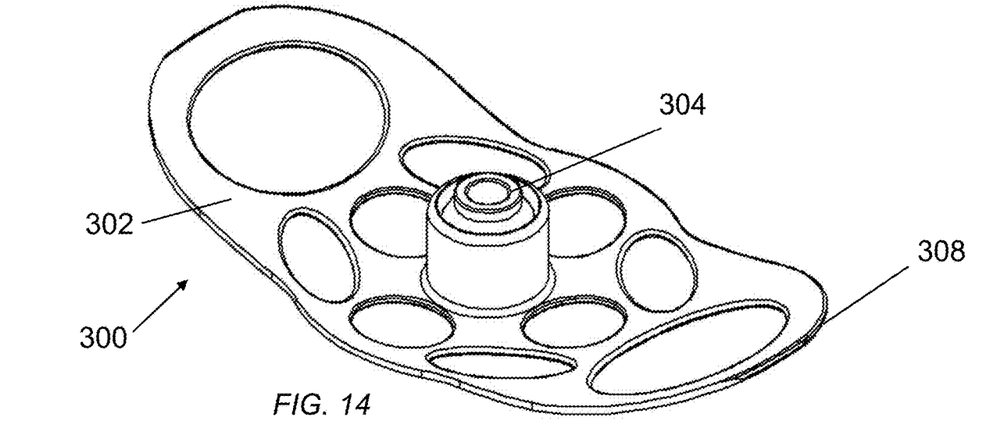
FIG. 14 is perspective view from above of the therapeutic apical base plate assembly in accordance with exemplary embodiments of the disclosed subject matter.
Figure 15:
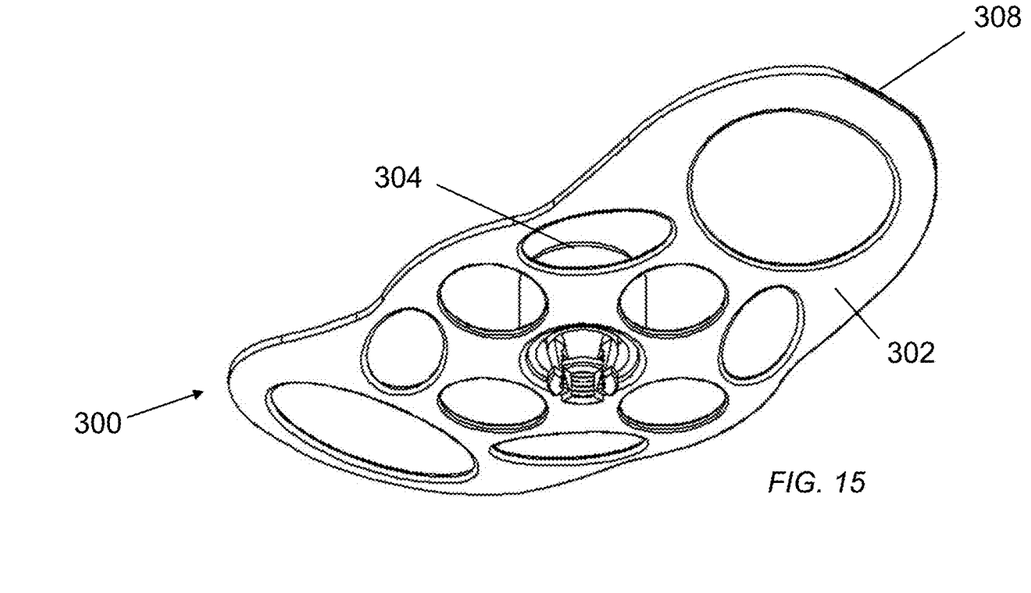
FIG. 15 is perspective view from below of the therapeutic apical base plate assembly in accordance with exemplary embodiments of the disclosed subject matter.

With reference to FIGS. 3, 6 and 7, flow channel directing ribs or ridges 126 are disposed on the surface of member 110. As illustrated in FIG. 3, ribs 126 run at angle 128 with respect to the longitudinal axis 130 of the member 110, and redirect the intercepted flow of blood onto and off of the valve leaflets, and facilitate proper vector upon entry into the ventricle VT. This hemodynamic re-vector restores the natural physiologic vector thereby facilitating the restoration of ventricular vortex, critical to physiologic healthy flow. Member 110 includes a fluid chamber, in which fluid is added or removed to increase or decrease the member 110 girth or width to increase or decrease the amount of transducted force captured from the atrioventricular pressure gradient, alter vector, adjust volume and/or velocity, and to create crescent-shaped articulation in the wings 114 of member 110, either anterior (see FIG. 6 or 7) or posterior (see FIG. 6 or 7), to better vector the intercept of atrial blood by introducing fluid into the 'wing' chambers.

As illustrated in FIGS. 8-11, the tethering conduit shaft 200 may include a plurality of concentric shafts, e.g., a movable shaft 202 and a fixed shaft 204. Shafts 202 and 204 are axially moveable with respect one another. An integrated inflatable axially adjusting reservoir or balloon 206 is supported at one end by shaft 204 and at the other end by shaft 202. Inflation of a reservoir or balloon by fluid introduced into reservoir or balloon 206 provides longitudinal movement of shaft 202 with respect to shaft 204, thereby facilitating placement of the member 110 with the ventricle and valve of the heart. With reference to FIG. 3, the introduction and/or removal of fluid from reservoir or balloon 206 allows adjustment of the location of the line of coaptation denoted by line 150 (longitudinal or axial adjustment). Shaft 208 is a multi-lumen shaft that maintains fluidic communication with member 110. In some embodiments, the inflatable reservoir or balloon 206 is sized, inflated, or adjusted to decelerate or accelerate inflow blood velocity by removing or offsetting excess ventricular volume facilitating the restoration of proper intracardiac flow.

FIGS. 12-15 illustrates the therapeutic apical base plate assembly 300 including the base plate 302 and a ball jointed portion 304 allowing for biased fixation. The base plate assembly is the delivery component of the captured and transducted energy and force of the atrioventricular pressure gradient into the ventricle VT, the ventricular walls, and the heart's H structures. In some embodiments, round oval cutouts 306 are defined in the base plate 302 to allow fibrous tissue in-growth for long term security.

Figure 16:
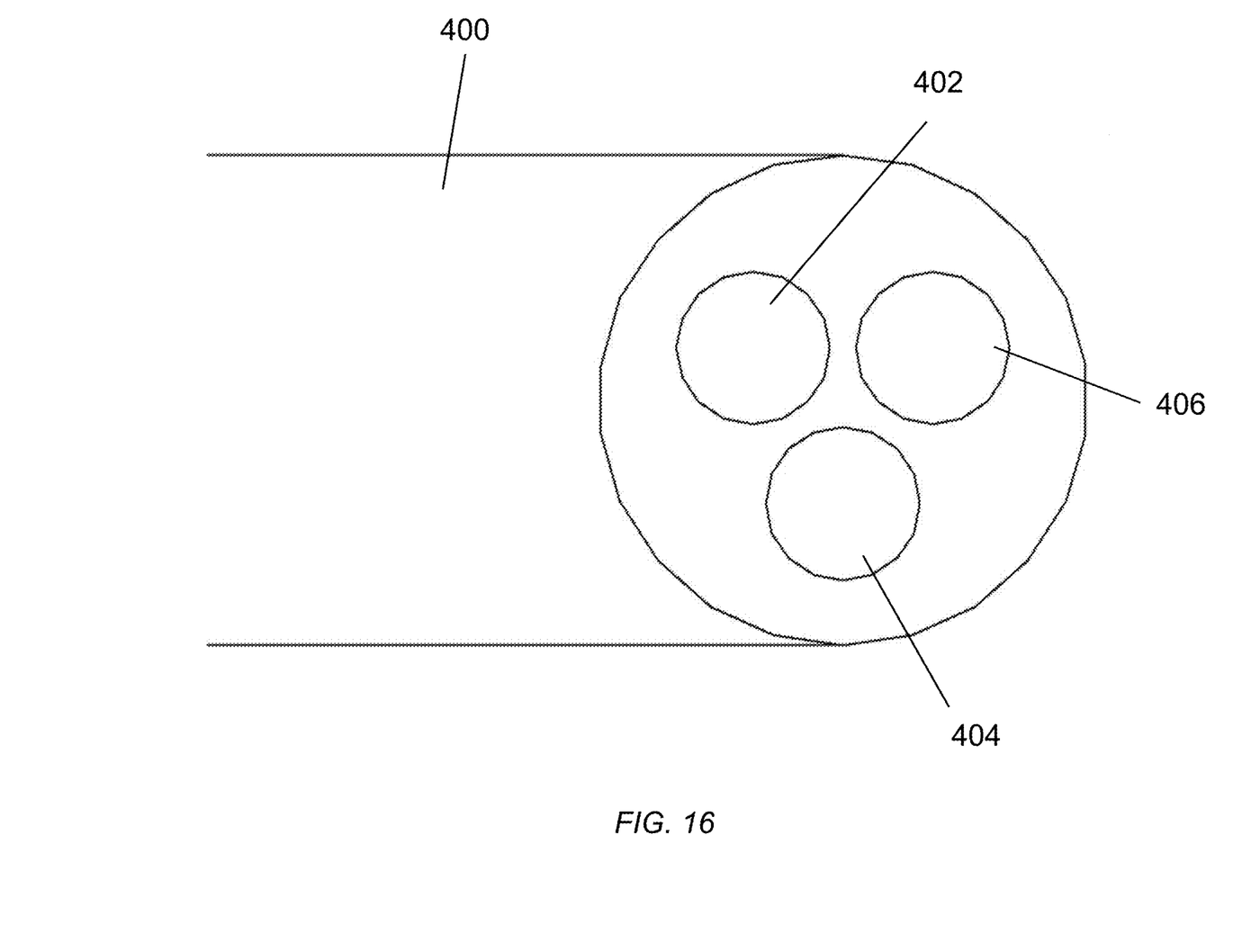
FIG. 16 is a view in partial section of the multi-lumen tube in accordance with exemplary embodiments of the disclosed subject matter.

With reference to FIGS. 3, 16, and 17, the control unit 600, which is implanted in the patient beneath the skin and capable of palpation by the surgeon, is provided to adjust the inflation and/or shape of member 110, and the adjustment assembly 800. In some embodiments, control unit 600 is provided with three independent contained chambers 602, 604 and 606, each identifiable below the skin in some embodiments by palpable protrusions, one palpable protrusion for chamber one 602, two palpable protrusions for chamber two 604, and three palpable protrusions for chamber three 606. A connection point 700 places the control unit 600 in fluid communication, via the tube 400 and shaft 200, with the member 110 and/or adjustment assembly 800. As illustrated in FIG. 16, tube 400 includes a plurality of lumens 402, 404, and 406 in respective fluid communication with chambers 602, 604 and 606. Control unit 600 has a needle access pad of silicone and/or ePTFE and/or non-porous, and/or any semi-porous material, which may allow fibrous tissue ingrowth (the body's method of preventing infection and facilitating hemostasis).

Figure 18:
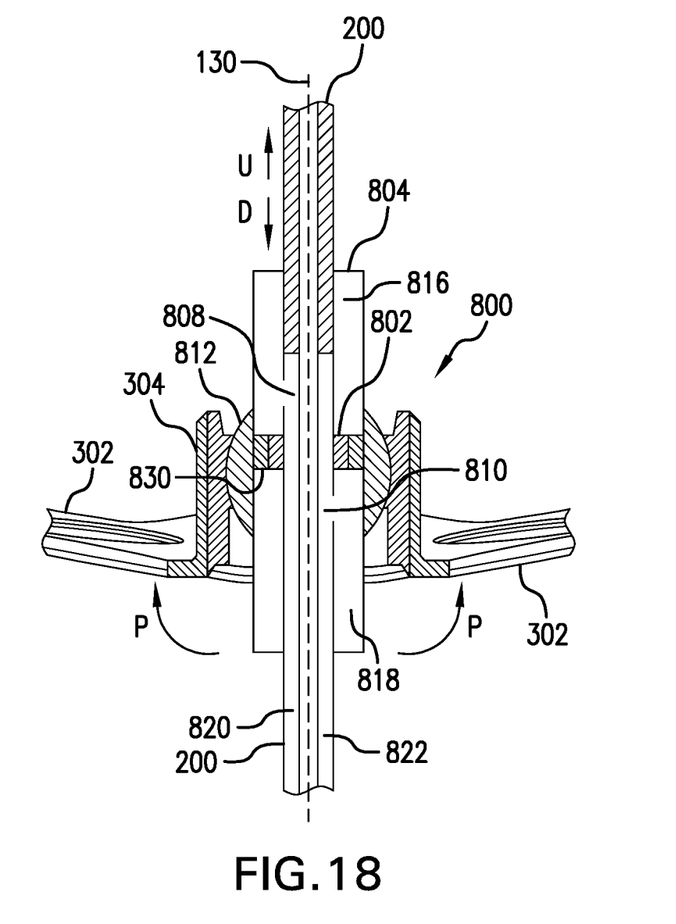
FIG. 18 is an enlarged cross section of the system in accordance with exemplary embodiments of the disclosed subject matter.

As illustrated in FIGS. 17-18, implant device 100 includes an adjustment assembly 800. In some embodiments, the adjustment assembly maintains the longitudinal position of the piston until pre-set force is exceeded by a change in cardiac force. In some embodiments, the adjustment assembly provides controllable longitudinal movement of the piston. The adjustment assembly can be a spring, fluidic valving, mechanical valving, electrical valving, and magnetic valving.

Adjustment assembly 800 includes a piston 802 contained inside a sealed fluid-filled housing 804. The housing 804 is positioned within or attached to apical/ventricular base plate 302. The piston 802 is attached to shaft 200 and is in fluid contact with subcutaneous control unit 600. Controlling fluid pressure on the piston 802 within the housing 804 enables controlled longitudinal movement or shaft length change (lengthening or shortening), which thereby raises or lowers (shortens or lengthens the distance between the attached distal device or component on one end and the apical/ventricular base plate 302 on the other end of the shaft 200) to affect the restoration and/or formation of an intracardiac vortex or to influence collection, compounding, and/or adjusting of the force and/or amount of the atrioventricular pressure gradient being collected, transducted, shifted, or moved for the specific purpose of therapeutically altering, replacing or augmenting the valvuo-ventricular interaction, the relationship, and the therapeutic interaction with the ventricular structures.

In some embodiments, piston 802 includes a sealing member 830 for maintaining a fluid seal between the piston 802 and the interior wall of the housing 804. Shaft 200 includes a plurality of lumens. For example, shaft 200 includes lumen 820 defining a distal opening 808 above piston 802, and a lumen 822 defining a proximal opening 810 below piston 802. Lumens 820 and 822 are in fluid contact with a subcutaneous control unit 600 accessible via fluid delivering needle to activate contained chambers 604 and 606.

The longitudinal adjustment, e.g., upward (arrow U) and downward (arrow D) along longitudinal axis 130, is produced changing the relative pressure between housing chambers 816, 818, located on either side of the piston 802. For example, adding fluid to the distal chamber 816 via opening 808 would cause the piston 1802 to be moved downward (arrow D), thereby lowering the device, e.g., member 110, attached to the shaft 200 (e.g., shortening the distance between the attached device on one end and the apical/ventricular base plate 302 on the other end of the shaft 200). Adding fluid to the proximal chamber 818 via opening 810, located below the piston 802, causes the piston to be moved upward (arrow U), thereby raising the device attached to the shaft 200 (e.g., lengthening the distance between the attached device on one end and the apical/ventricular base plate 302 on the other end of the shaft 200).

Moving the device or component attached to shaft 200 in a longitudinal manner, either up or down, changes position of the member or distal attachment along the line of coaptation to either change a flow vector or increase or decrease the amount of atrioventricular pressure gradient energy and force collected by increasing or decreasing the amount of exposed surface area of the implant by the moved shaft 200 attached to the distal device or component. Once the desired longitudinal adjustment has been achieved, locking stability is achieved by filling the opposite chamber 816, 818 to equalize the pressure in the two opposite chambers 816, 818 and hence hydraulically lock the piston 802, being fixed to the shaft 200, in place.

The housing 804 can be provided with a ball joint member 812 moveable with respect to a base 304 fixed to apical base plate assembly 300 that allows for pivotal movement (arrow P) of an attached device, with the hydraulically adjustable piston 802 allowing for longitudinal (upward/downward) adjustment all within the confines of the human heart. A biasing member, such as a spring (not shown), may be incorporated into the ball joint structure to bias the shaft 200 in an upright orientation, but allow lateral (e.g., pivotal) motion of the shaft.

Pivotal adjustment occurs as the housing 804 connected to base 304 via the 'ball joint' component 812 settles into a position determined by the native forces exerted by the human heart on the shaft-attached device. The distal chamber 816 and proximal chamber 818 may be in fluid contact with the distal and proximal surfaces of the piston 802, and thereby provide a resistive force to the piston 802, to control upward and downward movement. In some embodiments, the adjustment assembly includes a plurality of pistons, disposed inside a single housing, or a plurality of housings provided, such that each piston is disposed inside a housing.

Figure 19:
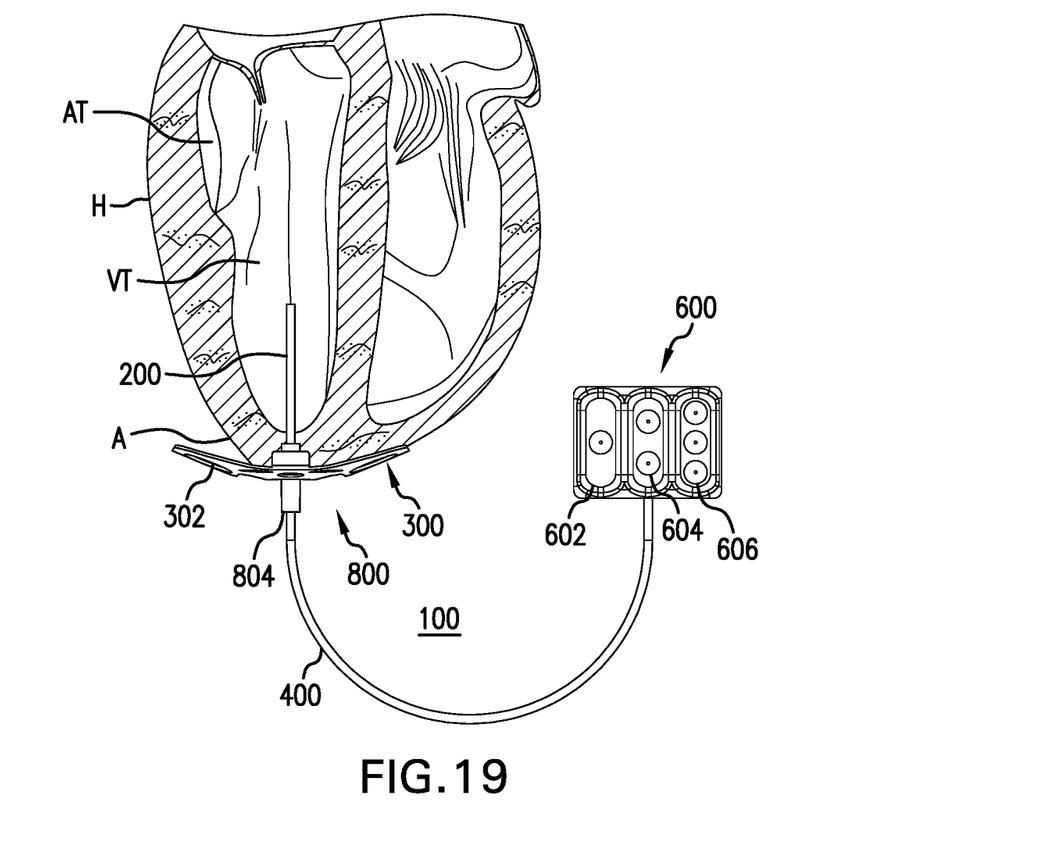
FIG. 19 is a side view of the system illustrated in-situ in the patient's heart in accordance with exemplary embodiments of the disclosed subject matter.

FIG. 19 illustrates the implant system 100 installed in the ventricle VT of the patient's heart H. (Implant 110 is not illustrated in the figure.) As discussed above, the transducting shaft 200 is designed to be fixed to the apex A of the heart H by a therapeutic apical base plate assembly 300.

Figure 20:
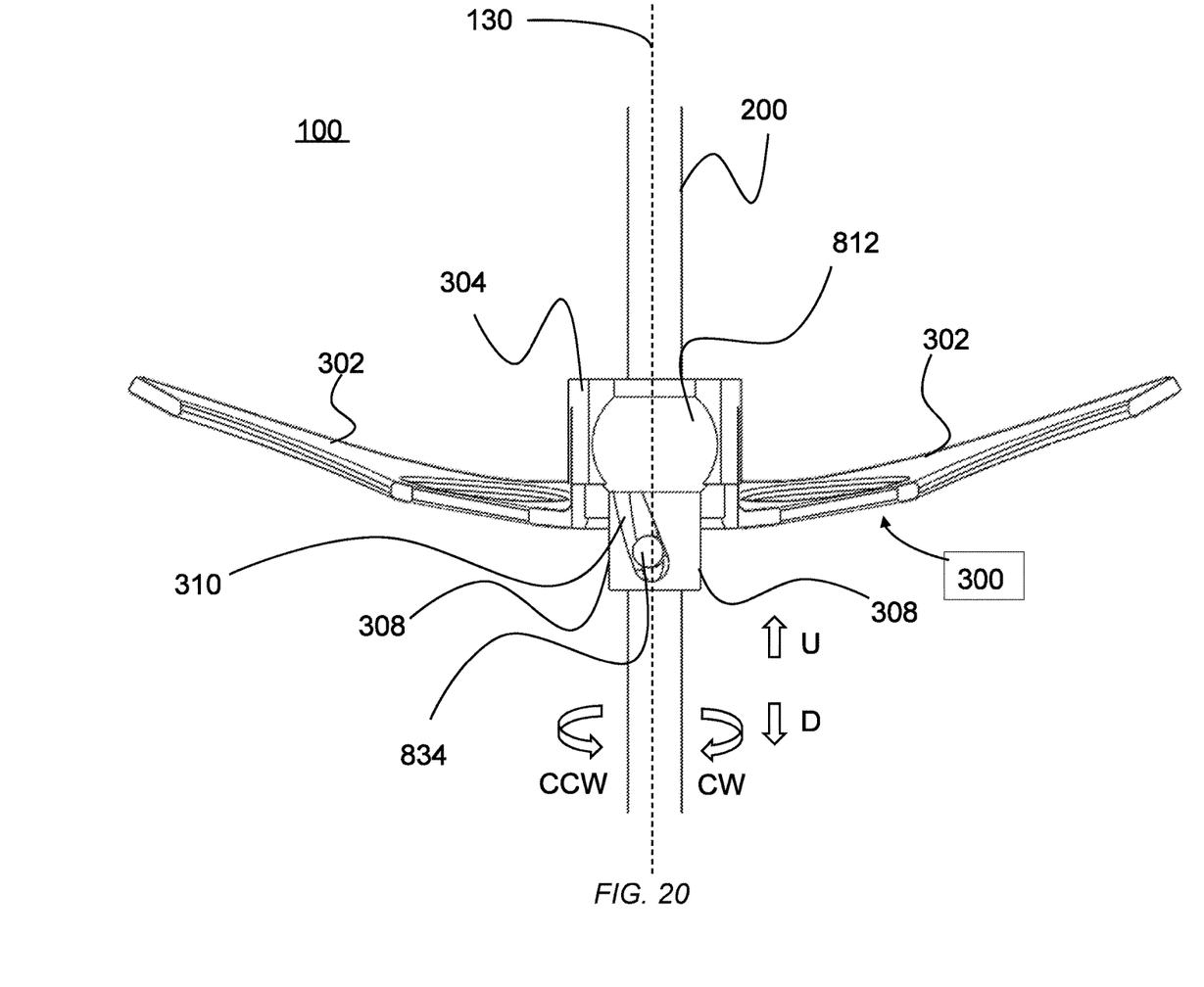
FIG. 20 is a side view in partial cross section of the system in accordance with another exemplary embodiment of the disclosed subject matter.

Another embodiment of the implant system 100 is illustrated in FIG. 20. Implant system 100 is substantially identical to implant system 100, with the differences noted herein. For example, the base 304 includes a lower portion 308 provided with a spiral-shaped channel or slot 310. Lower portion 308 is rigidly attached to plate 302 of apical anchoring system 300. The shaft 200, to which piston 802 is attached (not shown in FIG. 20), includes a pin 834 that extends radially outward from the shaft 200' and which is slidable within the slot 310, so as the shaft 200 moves longitudinally (arrows U and D), movement of the pin 834 within the slot 310 invokes angular rotational motion (arrows CW and CCW) to the shaft 200 about the longitudinal axis 130. The implant system of claim 27, wherein the direction of the spiral slots is oriented to deliver and twist or counter-twist to the apex of the heart driven by the implant, as a force transduction therapy. The direction of the spiral slots is oriented to deliver a twist or counter-twist to the apex A of the heart H driven by the cycles of diastole & systole, the atrioventricular pressure gradient (pressure differential), and the valvular position of the implant, as a force transduction ventricular therapy, with the intent to reverse (positively) remodel and/or restore geometric shape to a ventricle.

The implant device can be used to position an implant or distal attachment in, above, or below a valve orifice or between valve leaflet to effect the vector at which blood flows through the valve orifice and/or flows off of the native or prosthetic valve leaflets and/or preserve or enhance the atrioventricular pressure gradient. The piston is operative to move a structure, component, or device (such as implant 110) in, above, or below a valve orifice or between valve leaflet to effect, change, or amplify a native or prosthetic force applied to a native or prosthetic structure, a native or prosthetic component, or prosthetic device.

It will be appreciated that the methods and systems described above are set forth by way of example and not of limitation. Numerous variations, additions, omissions, and other modifications will be apparent to one of ordinary skill in the art. Thus, while particular embodiments have been shown and described, it will be apparent to those skilled in the art that various changes and modifications in form and details may be made therein without departing from the spirit and scope of this disclosure and are intended to form a part of the disclosure as defined by the following claims, which are to be interpreted in the broadest sense allowable by law.

What is claimed is:

1. An implant system for improving intracardiac blood flow, the implant system comprising:
   a first shaft comprising a proximal end, a distal end, and a first lumen and a second lumen extending therethrough;
   a second shaft comprising a proximal end and a distal end;
   a flow-vectoring member coupled to the distal end of the second shaft, the flow vectoring member comprising an inflatable paddle disposed at a distal-most end of the member, wherein the flow-vectoring member comprises a chamber for receiving an inflating fluid;
   an adjustment assembly coupled to the proximal end of the second shaft and the distal end of the first shaft; and
   an apical base coupled to the adjustment assembly;
   wherein the adjustment assembly comprises:
      a housing having a fluid disposed therein, wherein the first lumen and the second lumen do not extend beyond the housing;
      a piston slidably disposed inside the housing coupling the first shaft to the second shaft, the piston sealably dividing the housing into a distal chamber and a proximal chamber, the distal chamber is in fluid communication with the first lumen via a first opening in the first shaft and the proximal chamber is in fluid communication with the second lumen via a second opening in the first shaft, wherein adjusting fluid pressure acting on the piston thereby increases or decreases a length between the flow vectoring member and the apical base plate; and a joint portion comprising a ball joint coupled between the housing and the apical base plate, wherein the joint portion is configured to adjust an angle of the apical base plate relative to the housing.

2. The implant system of claim 1, further comprising:
a control unit coupled to the proximal end of the first shaft and in fluid communication with the plurality of lumens; and
wherein the fluid is further disposed within the flow-vectoring member, the first shaft, the second shaft, and the control unit.

3. The implant system of claim 1, further comprising a crescent beam disposed at a distal end of the flow-vectoring member, a first side wing having a crescent-shaped articulation, a second side wing having a crescent-shaped articulation, and a truss extending from the crescent beam to the second shaft.

4. The implant system of claim 3, wherein the first side wing comprises a first rib extending outwardly and the second side wing comprises a second rib extending outwardly, each rib configured to channel blood flow.

5. The implant system of claim 1, wherein the second shaft further comprises an inflatable balloon disposed between the apical base plate and the flow-vectoring member.

6. The implant system of claim 1, wherein the inflatable paddle comprises a wider distal portion and tapers proximally to a narrow portion.

7. The implant system of claim 1, wherein the chamber is one of a plurality of chambers for receiving an inflating liquid.

8. The implant system of claim 1, wherein the adjustment assembly comprises a spring, a fluidic valve, a mechanical valve, an electrical valve, or a magnetic valve.

9. The implant system of claim 1, wherein the apical base plate comprises a plurality of cutouts configured to allow fibrous tissue in-growth.

10. The implant system of claim 1, wherein the apical base plate comprises a slot within the base.

11. The implant system of claim 1, wherein the apical base plate comprises an inflatable structure.

12. The implant system of claim 1, wherein the apical base plate comprises an expandable structure.

13. The implant system of claim 10, wherein the second shaft further comprises a pin disposed within the slot.

14. The implant system of claim 1, wherein the second shaft is one of a plurality of concentric shafts, the plurality of concentric shafts comprising a fixed shaft and a movable shaft.

15. The implant system of claim 1, wherein the ball joint comprises a shaft retention feature.

16. The implant system of claim 1, wherein the control unit comprises a plurality of access sites.

17. The implant system of claim 1, wherein the control unit comprises a plurality of fluid reservoirs.

18. The implant system of claim 1, wherein increasing pressure of the fluid in the distal chamber of the housing increases the length between the flow vectoring member and the apical base plate.

19. The implant system of claim 1, wherein increasing pressure of the fluid in the proximal chamber of the housing decreases the length between the flow vectoring member and the apical base plate.

20. The implant system of claim 1, further comprising a third lumen extending through the first shaft and the second shaft and in fluid communication with the flow-vectoring member.

* * * * *